(12) United States Patent
Kim et al.

(10) Patent No.: US 6,946,143 B2
(45) Date of Patent: Sep. 20, 2005

(54) MEDICAL MATERIALS AND POROUS SCAFFOLDS FOR TISSUE ENGINEERING MADE FROM THE BIODEGRADABLE GLYCOLIDE/ε-CAPROLACTONE COPOLYMER

(75) Inventors: Young-Ha Kim, Seoul (KR); Soo-Hyun Kim, Seoul (KR); Ki-Dong Park, Seoul (KR); Sung-Won Choi, Seoul (KR); Soo-Hong Lee, Seoul (KR); Il-Keun Kwon, Busan (KR)

(73) Assignee: Korea Institute of Science and Technology, Seoul (KR)

( * ) Notice: Subject to any disclaimer, the term of this patent is extended or adjusted under 35 U.S.C. 154(b) by 443 days.

(21) Appl. No.: 10/144,813

(22) Filed: May 13, 2002

(65) Prior Publication Data

US 2003/0215483 A1 Nov. 20, 2003

(51) Int. Cl.$^7$ .............................. A61F 16/00; A61K 9/70
(52) U.S. Cl. ....................... 424/443; 424/444; 424/422; 424/423
(58) Field of Search ................................ 424/443, 444; 521/82, 61

(56) References Cited

U.S. PATENT DOCUMENTS

| 4,700,704 A | 10/1987 | Jamiolkowski et al. | |
|---|---|---|---|
| 5,133,739 A | * 7/1992 | Bezwada et al. | ............ 606/230 |
| 5,677,355 A | * 10/1997 | Shalaby et al. | ................ 521/61 |
| 6,306,424 B1 | * 10/2001 | Vyakarnam et al. | ......... 424/426 |

OTHER PUBLICATIONS

Alger, M., ed. Polymer Science Dictionary, 2nd ed., 1997, pp. 265 and 290. Chapman & Hall (London).*

* cited by examiner

*Primary Examiner*—Sandra E. Saucier
*Assistant Examiner*—Lora E Barnhart
(74) *Attorney, Agent, or Firm*—Jones Day (57) ABSTRACT

Disclosed is a biocompatible medical material and porous scaffold for use in tissue engineering, made from a biodegradable glycolide/ε-caprolactone copolymer having a repeat unit of

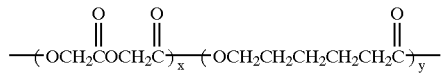

wherein x and y are integers greater than or equal to 18, the copolymer has an average molecular weight of about 10,000 daltons or more, and the molar ratio of glycolide:ε-caprolactone in the copolymer is about 4.0:6.0 to 6.0:4.0.

5 Claims, 3 Drawing Sheets

----- lactide/glycolide copolymer

——— glycolide / $\varepsilon$-caprolactone copolymer

MEDICAL MATERIALS AND POROUS SCAFFOLDS FOR TISSUE ENGINEERING MADE FROM THE BIODEGRADABLE GLYCOLIDE/ε-CAPROLACTONE COPOLYMER

FIELD OF THE INVENTION

The present invention relates to medical materials and porous scaffolds for tissue engineering made from a biodegradable synthetic polymer having superior mechanical and appropriate hydrolytic properties. More particularly, the present invention relates to biodegradable medical materials and porous scaffolds for tissue engineering made from a glycolide/ε-caprolactone copolymer, and the medical materials and porous scaffolds have excellent mechanical properties such as good flexibility and elasticity, proper hydrolytic properties, and uniform pore size and distribution.

BACKGROUND OF THE INVENTION

Major requirements for materials used as a substrate or a scaffold for the regeneration of human tissues are promotion of excellent cell adhesion and proliferation, and maintenance of integrity for the differentiated cell functions. Furthermore, the materials should be well deliquesced with contiguous tissues after transplantation without inflammatory reaction, and they should self-deteriorate after a predetermined period so that they do not remain in vivo as gratuitous materials.

Known, conventional materials having acceptable absorption rates in the living body include natural and synthetic polymers such as collagen, gelatin, hyaluronic acid, pectin, and cellulose derivatives. The porous scaffolds were introduced for the purpose of cell or tissue culture and transplantation, cosmetics, medical materials such as wound coverings and dental matrix. Among these various uses, Japanese patent laid-open No. 7-313585 discloses a method for manufacturing scaffolds using hyaluronic acid, wherein the hyaluronic acid scaffolds, cross-linked by an epoxy compound and thrombin-added hyaluronic acid, are used as wound coverings. In addition, WO 94/02517 suggests a method for manufacturing insoluble hyaluronic acid derivate scaffolds through cross-linking of carbodiimide.

However, those scaffolds manufactured by using only hyaluronic acid are easy to break, and they are very soluble in water or in body fluids unless they are cross-linked. Therefore, cross-linking materials such as divinylsulfone, formaldehyde, carbodiimide and epoxy compounds have to be used for providing the mechanical properties necessary for manufacturing scaffolds. Since unreacted divinylsulfone and aldehyde cause cytotoxicity in the living body, use of the same are restricted.

Natural polymers have the advantage of source as natural substances so that they are inherently compatible to a living body. However, there are disadvantages such as relatively high tissue rejection reactivity and infection rate, and it is difficult to control their decomposition properties. Also, there have been reports that their mechanical properties are weak in an aqueous environment.

Thus, active studies on biodegradable synthetic polymers have been carried out. The basic structure of a biodegradable synthetic polymer consists of an absorbable structure and a degradable structure; structures capable of hydrolysis are used for the latter. Aliphatic polyesters having excellent physical characteristics and hydrolysis property are proposed for materials as biodegradable synthetic polymers. Currently used biodegradable synthetic polymers are polyamino acid, polyanhydride, polycaprolactone, polyglycolide, polylactide and their derivatives, i.e., lactide and glycolide copolymers.

Currently porous polymeric scaffolds using biodegradable polymers such as polyglycolide, polylactide, lactidelglycolide copolymer are commonly used. However, they have limited physical properties which puts great limitations as use for regeneration materials for human tissue or organ, which requires versatile physical properties. Especially, elasticity is an essential property for muscular tissues constituting skeletal muscles, smooth muscles, heart muscles and the like, and the elastic scaffold materials are expected to have distinguished effects in the regeneration of such elastic tissues.

Further, there have been reports that mechanical stimulation during culture of cell lines in a scaffold makes the cells stronger, which is very advantageous in tissue regeneration (B. S. Kim, J. Nikolovski, E. Smiley, J. Bonadio and D. J. Mooney, Bioengineering Conference, 42, 27~28, 1999).

Biodegradable polymers such as polyglycolide and polycaprolactone have low immunity and negligible toxicity, and is suitable for medical uses. In particular, poly-glycolides have superior mechanical properties (D. L. Wise et al., "Drug Carries in Biology and Medicine", 1st ed., G. Gregoriadis, Ed., Academic Press, New York, 237–270, 1979).

On selecting biodegradable polymeric materials for preparing a porous scaffold for tissue engineering, one must consider that the materials should cause the growth of the cells in tissue, maintain the function of differentiated cells, be well deliquesced with contiguous tissues after transplantation without inflammatory reaction, and should self-deteriorate after a predetermined time so that they do not remain in vivo as gratuitous materials.

SUMMARY OF THE INVENTION

The present invention follows extensive study of various biodegradable synthetic polymers in order to develop biodegradable synthetic polymeric scaffolds and medical materials having excellent mechanical properties such as flexibility and elasticity. The present invention is the result and is directed to a glycolide/ε-caprolactone copolymer made by copolymerizing glycolide and ε-caprolactone with composition ratios appropriately controlled, which has the superior elasticity of a poly-glycolide and superior flexibility of a polycaprolactone. Thus, the present copolymers have excellent mechanical properties such as flexibility and elasticity, and also provide appropriate biodegradation time so that they can be used in manufacturing bio-degradable porous polymeric scaffolds suitable for regeneration of soft tissues such as skin and blood vessel, and medical materials such as medical matrix and wound coverings.

The inventive concept is for a porous scaffold for tissue engineering made from a biodegradable glycolide/ε-caprolactone copolymer which has a repeat unit of Formula 1,

[Formula 1]

glycolide/ε-caprolactone copolymer wherein x and y are each integers greater than or equal to 18. The inventive co-polymer has an average molecular weight of about 10,000 daltons or more.

The present porous scaffold has a molar ratio of glycolide:ε-caprolactone in glycolide/ε-caprolactone copolymer of about 2.0:8.0 to 8.0:2.0; and has an average pore size of about 1 to 800 μm The porous scaffold has a porosity of about 50 to 99%. Preferably, the porous scaffold has an average pore size of about 200 to 500 μm and porosity of about 93 to 96%. The porous scaffold is used, inter alia, for tissue cell cultures and tissue regeneration such as for artificial skin grafts and prosthetic blood vessels.

Another embodiment of the present invention includes a biocompatible material for medical use manufactured from a biodegradable copolymer of glycolide and ε-caprolactone. The present biocompatible material for medical use is comprised of the bio-degradable glycolide/ε-caprolactone copolymer having a repeat unit of Formula 1, as described above. The present biocompatible material has a molar ratio of glycolide:ε-caprolactone in glycolide/ε-caprolactone copolymer of about 2.0:8.0 to 8.0:2.0 and is used, inter alia, for dental matrix and wound coverings.

BRIEF DESCRIPTION OF DRAWINGS

FIGS. 3a through 3d are Scanning Electron Microscope (SEM) photographs which show the surface characteristics of the porous scaffold made from the present glycolide/ε-caprolactone copolymer.

DETAILED DESCRIPTION OF THE PRESENT INVENTION

Preferred embodiments of the present invention will now be described with references to the accompanying drawings.

As described above, the glycolide/ε-caprolactone copolymer used in porous scaffolds and medical materials, has a repeat unit of Formula 1, and is a biodegradable copolymer with flexibility and elasticity having an average molecular weight of approximately 10,000 daltons or more.

[Formula 1]

—(OCH$_2$COCH$_2$C)$_x$—(OCH$_2$CH$_2$CH$_2$CH$_2$CH$_2$C)$_y$— glycolide/ε-caprolactone copolymer

In Formula 1, x and y stand for the degree of polymerization, i.e. the number of repeating units of glycolide and ε-caprolactone monomer. As noted above, the preferred number on repeat units are at least 18.

The glycolide/ε-caprolactone copolymer has a translucent brown color, and it has excellent elasticity and flexibility and appropriate hydrolytic property, which is very useful for manufacturing of porous scaffolds for tissue engineering and medical materials.

Appropriate molar ratios of glycolide:ε-caprolactone in the glycolide/ε-caprolactone copolymer used in the present invention, are between 2.0:8.0~8.0:2.0. If the molar ratio of glycolide in the copolymer is greater than 80%, the modulus of the resultant copolymer is excessively high and a porous scaffold made from such a co-polymer is too rigid, while if the molar ratio thereof is less than 20%, it is too soft and the scaffold structure may collapse. Further, if a scaffold is made from a glycolide/ε-caprolactone copolymer having a molecular weight of less than 10,000, its mechanical strength is too weak.

The glycolide/ε-caprolactone copolymer used herein can be manufactured through ring-opening polymerization carried out by heating glycolide and ε-caprolactone under reduced pressure in the presence of a polymerization catalyst.

An exemplary manufacturing process for the glycolide/ε-caprolactone copolymer of the present invention will now be described. The glycolide/ε-caprolactone copolymer having a repeat unit of the formula 1 is manufactured according to a copolymerization reaction as expressed by scheme 1 below:

[Scheme 1]

The ring-opening polymerization reaction is performed by heating the monomers under reduced pressure with the use of ring-opening polymerization catalyst. The reaction temperature ranges about 100~230° C., and preferably about 150~200° C. and the reaction time is about at least 5 hours, and preferably about 5~100 hours, and particularly about 5~50 hours.

All known catalysts used generally in ring-opening polymerization reactions of glycolide and ε-caprolactone may be used in the polymerization. The catalysts used in the ring-opening polymerization are tetraphenyl tin, tin powder, stannous octoate, stannous chloride, stannic chloride, tin oxide, zinc powder, diethyl zinc, zinc octoate, zinc chloride and zinc oxide, etc. The amount of the catalyst to be added is approximately 0.0001~5 mol %, and preferably 0.001~0.5 mol % with respect to amounts of glycolide and ε-caprolactone.

The molecular weight of the copolymer is increased as the polymerization reaction proceeds. Analyzing the copolymer structure and measuring the molecular weight are performed by means of a hydrogen nuclear magnetic resonance ($^1$H-NMR) spectroscopy, a Differential Scanning Calorimetry (DSC) and Gel Permeation Chromatography (GPC).

The glycolide/ε-caprolactone copolymer having a repeat unit of the above Formula 1 in the present invention, which is used in the manufacturing of porous scaffolds for tissue engineering and materials for medical purposes, can freely transform its physical shape compared with conventional biodegradable polymers such as polyglycolide, polylactide, lactide/glycolide copolymer and the like, and it also has excellent elasticity that overcomes limitation of mechanical properties of the conventional biodegradable polymers. Further, scaffolds manufactured from the conventional lactide/glycolide copolymer have the slight elasticity that is the major shortcoming for performing mechanical stimulation in the cell culture, while the scaffold prepared by glycolidele-caprolactone copolymer of the present invention has great elasticity capable of regenerating tissue under continuous mechanical stimulation in cell culture.

The porous scaffolds for tissue engineering of the present invention can be manufactured according to various methods by using glycolide/ε-caprolactone copolymer having a repeat unit of the Formula 1.

The above mentioned methods are as follows: solvent-casting/particle-leaching method, wherein a polymeric solution mixed with salt particle is dried and salt is dissolved in water [A. G. Mikos et al., Polymer, 35, 1068 (1994)]; gas foaming method, wherein polymer is expanded by using $CO_2$ gas [L. D. Harris et al., J. Biomed. Mater. Res., 42, 396(1998)]; gas foaming salt method, wherein a polymeric solution mixed with foaming salt are dried and the foaming salt is foamed in water or in an acid solution to manufacture scaffolds [Y. S. Nam et al., J. Biomed. Mater. Res., 53, 1 (2000)]; fiber extrusion and fabric forming process, wherein non-woven fabric is manufactured by using a polymeric fiber and is prepared in the form of a polymeric sieve [K. T. Paige and C. A. Vacanti, Tissue Engineering, 1, 97 (1995)]; thermally induced phase preparation method, wherein a solvent contained in a polymeric solution is phase-separated by impregnating it in a nonsolvent [C. Schugens et al., J. Biomed. Mater Res., 30, 449 (1996)]; and emulsion freeze-drying method, wherein an emulsion of a mixture of a polymeric solution and a nonsolvent is rapidly frozen and freeze-dried in liquid nitrogen [K. Whang, Polymer, 36, 837 (1995)].

The method for manufacturing the porous scaffold for tissue engineering from glycolide/ε-caprolactone copolymer of the present invention will be discussed in detail with reference to the above-mentioned method using the foaming salt and the emulsion freeze-drying method.

According to the method using the foaming salt, ammonium bicarbonate crystals of a predetermined size as a foaming salt are mixed uniformly with about 10% by weight of glycolide/ε-caprolactone copolymer solution which is manufactured by using chloroform or methylene chloride solvent, and the mixture are pressed into a teflon-coated mold having a selected shape. After solvent is volatized, there is manufactured a sample of the porous scaffold consisting of foaming salt and polymeric materials. This sample is foamed three times for approximately 20 minutes once in an alcohol aqueous solution of approximately 50% by weight and in an aqueous solution of citric acid of approximately 50% by weight in turns. Afterwards, the sample is put in a bath of approximately 50° C. for approximately two days with distilled water exchanged at every six hours in order that remaining ammonium bicarbonate, alcohol and citric acid are removed. The sample is freeze-dried to manufacture the porous scaffolds consisting of the glycolide/ε-caprolactone copolymer.

According to the emulsion freeze-drying method, 10 g of approximately 5% of glycolide/ε-caprolactone copolymer solution and distilled water is mixed in the weight ratio of approximately 60:40, and an emulsion is prepared by using an ultrasound mixer. This emulsion is poured promptly into a teflon-coated mold having a selected shape and is instantaneously freeze-dried by putting it in a liquid nitrogen of −196° C. The resultant is then stored in a room temperature for one day and dried by a freeze dryer to manufacture a porous scaffold consisting of the glycolide/ε-caprolactone copolymer.

In addition to the above-described methods, various methods described in the above can be used including a method for expanding polymers by using the $CO_2$ gas in order to manufacture the porous scaffold for tissue engineering from the glycolide/ε-caprolactone copolymer of the present invention.

An ideal shape of porous scaffold manufactured by using the glycolide/ε-caprolactone copolymer of the present invention makes it possible to obtain formation of pores having predetermined average sizes, high internal connectivity and appropriate mechanical strength. Pore size and porosity of the scaffold are controlled by varying manufacturing methods, whereby the entire shape of the scaffold is determined.

Influences of the pore size and porosity on the shape of the scaffold are discussed hereinafter. The scaffold has the optimal shape when the pore size is approximately 200~500 μm, and the shape of the scaffold is also excellent when the size is 50~200 μm or 500~800 μm. If the size is approximately 1~50 μm, the shape of the scaffold is not so good. In that case, however, the shape of the scaffold is still sufficient to act as a scaffold. If the size is below approximately 1 μm, salt within the scaffold is hardly extracted and the internal connectivity of a manufactured scaffold is inferior. If the size is over about 800 μm, the mechanical strength of the scaffold is too weak and is not suitable as a scaffold.

With regard to the porosity, the scaffold has the optimal shape when the porosity is approximately 93~96%, and the shape is also excellent when the porosity is approximately 80~93% or approximately 96~99%. If the porosity is approximately 50~80%, the scaffold does not have good shape. In that case, however, the scaffold still has sufficient shape to function as a scaffold. If the porosity is below approximately 50%, the internal connectivity of the pore is inferior. If the porosity is over about 99%, the mechanical strength of the scaffold is too weak and is not suitable as a scaffold.

The pore size has a complementary relation to the porosity to control the shape of the scaffold, and the optimal shape of the scaffold is obtained when the pore size is approximately 200~500 μm, and the porosity is approximately 93~96%.

The porous scaffold for tissue engineering made from the glycolide/ε-caprolactone copolymer according to the present invention is useful for adhesion and growth of vascular endothelial cells or skin tissue cells, and it is also useful for manufacturing artificial organs since the scaffold is spontaneously biodegradable and is absorbed into living body after completing the cell growth.

Furthermore, the biodegradable porous scaffold manufactured by using the glycolide/ε-caprolactone copolymer of the present invention is applicable to all organ tissues which are recoverable, such as artificial skin, artificial blood vessel and artificial liver.

The present invention will now be discussed in detail with reference to the following examples and examples. However, it is to be noted that the present invention is by no means limited to these examples.

EXAMPLE 1

Lactide of 15.900 g and glycolide of 8.550 g were reacted in a dried glass ampoule of 100 ml in volume in the presence of stannous octoate of 0.0099 g diluted in toluene of 0.070 ml. A teflon-coated magnetic bar was introduced in the ampoule, and the ampoule was kept in vacuum state at 0.01 mmHg for 2 hours to remove toluene and water. Injection of dried nitrogen and application of the vacuum state were performed three times, and the ampoule is thermally sealed. The thermally sealed ampoule was stirred by using a magnetic plate in an oil bath of 100° C. by raising the temperature to 150° C. in rate of 1° C./min.

Subsequently, solid phase polymerization was performed at temperature of 150° C. for 20 hours. As the polymerization was processed, viscosity of polymerization system was raised and the agitation was available no more. At first, the polymerization system was in a transparent gel state, but it was altered to a translucent solid of ivory color as the polymerization proceeded. After completing the polymerization, the ampoule was sufficiently cooled by using liquid nitrogen, and it was destroyed to collect copolymers. Collected samples were dissolved in chloroform and then precipitated in methanol to remove unreacted monomers and the catalyst. The obtained samples were vacuum-dried at room temperature for 24 hours and vacuum-packed, and then it was stored at −25° C. In this way, copolymer of 24.083 g was obtained (yield: 98.5%).

From the GPC analysis in that chloroform was used as a mobile phase solvent with a flow rate of 1 ml/min at 30° C., weight-average molecular weight and distribution of molecular weight of the copolymer were identified to be about 226,000 and 1.50, respectively. Analyzed by the $^1$H-NMR method, the molar ratio of lactide:glycolide in the copolymer was 6.0:4.0, and determined through the DSC, the glass transition temperature (Tg) was 52.94° C.

EXAMPLE 2

The lactide/glycolide copolymer obtained in Example 1 was homogeneously dissolved in a chloroform solution by using a magnetic stirrer so that it becomes a 4% solution. Manufactured polymeric solution of 22.5 g was added in a vial, and salt particle (NaCl salt) of ψ 200~300 μm of 17.1 g was added to make the porosity as 95%. They were mixed uniformly by means of a small-sized mixer. The mixed solution was poured in a mold and dried for 24 hours. After the volatilization of all solvent, a disk type sample including the salt particle was washed several times with ultra pure water to remove the salt particle. At this time, the ultra pure water was changed at every six hours for two days so that the remaining salt within the sample was completely removed. Afterwards, the solution was freeze-dried.

According to Scanning Electron Micrograph (SEM) analysis on the size and distribution of pore of the porous scaffold as manufactured above, shape and distribution of pore of outer surface and internal section of the scaffold were almost identical, and control of pore distribution can be achieved by controlling size and amount of salt particle.

Mechanical properties of the manufactured scaffold were analyzed by using a universal testing machine. At first, the manufactured scaffold was uniformly cut into 10×10 mm samples and the samples were attached on a fixed plate so that they could be maintained in measuring length of 7 mm. Using a load of 5 kg through a cell, tensile strength of the sample was measured at uniform speed of 1 mm/min. As a result, the elongation, the tensile strength and the modulus were 28%, 0.28 Mpa and 2.5 Mpa, respectively.

EXAMPLE 3

Glycolide of 1.935 g and ε-caprolactone of 17.123 g were reacted in a dried glass ampoule of 100 ml in volume in the presence of stannous octoate of 0.0090 g diluted in toluene of 0.064 ml. A Teflon-coated magnetic bar was introduced in the ampoule filled with the reactants, and the ampoule was kept in vacuum state at 0.01 mmHg for 2 hours to remove toluene and water. Injection of dried nitrogen and application of the vacuum state were performed three times, and the ampoule was thermally sealed. The thermally sealed ampoule was agitated by using a magnetic plate in an oil bath of 90° C. by raising the temperature to 170° C. in rate of 1° C./min.

Subsequently, solid phase polymerization was performed at temperature of 170° C. for 20 hours. As the polymerization was processed, viscosity of polymerization system was raised and the agitation was available no more. At first, the polymerization system was in a transparent gel state, but it was altered to a solid of gold color as the polymerization proceeded. After completing the polymerization, the ampoule was sufficiently cooled by using liquid nitrogen, and it was destroyed to collect copolymers. Collected samples were dissolved in chloroform and then precipitated in methanol to remove unreacted monomers. In this way, copolymer of 18.334 g was obtained (yield: 96.20%).

From the GPC analysis in that chloroform was used as a mobile phase solvent with a flow rate of 1 ml/min at 30° C., weight-average molecular weight and distribution of molecular weight of the copolymer were identified to be 213,000 and 1.64, respectively. Analyzed by the $^1$H-NMR method, the molar ratio of glycolide:ε-caprolactone in the copolymer was 1.0:9.0, and determined through the DSC, the glass transition temperature (Tg) and the melting point Tm were 53.2° C. and 58.0° C., respectively.

Using the copolymer as manufactured above, a porous scaffold having porosity 95% and pore size ψ 200~300 μm was manufactured according to the same manufacturing process as in Example 2. According to the same measuring method as in Example 2, the mechanical properties of the scaffold were determined. The elongation, the tensile strength and the modulus were 920%, 0.07 Mpa and 0.368 Mpa, respectively.

The modulus of this scaffold was excessively high and the scaffold was unduly rigid. This scaffold is not suitable for regeneration of flexible tissues.

EXAMPLE 4

According to the same manufacturing process as in Example 3, a glycolide/ε-caprolactone copolymer was manufactured by using glycolide of 17.111 g and ε-caprolactone of 1.903 g with a catalyst of stannous octoate of 0.0089 g diluted in toluene of 0.062 ml.

As the composition ratio of glycolide in the collected glycolide/ε-caprolactone copolymer sample was high, it was not soluble in chloroform. Therefore, it was dissolved in hexafluoroisopropanol and precipitated in methanol to remove unreacted minute monomers. Yield of the copolymer was 98.4%. Intrinsic viscosity of the collected copolymer was 1.68 dl/g when it was measured from 0.5 g/dl hexafluoroisopropanol solution at 25° C. Analyzed by the $^1$HNMR method, the molar ratio of glycolide:ε-caprolactone in the copolymer was 9.0:1.0, and determined through the DSC, the glass transition temperature (Tg) and the melting point were 22.7° C. and 217.1° C., respectively.

After the copolymer as manufactured above was dissolved in hexafluoro-isopropanol, a porous scaffold having porosity of 95% and pore size of ψ 200~300 μm was manufactured according to the same manufacturing process as in Example 2. According to the same measuring method as in Example 2, the mechanical properties of the scaffold were determined. The elongation, the tensile strength and the modulus were 19%, 0.85 Mpa and 5.01 Mpa, respectively.

The modulus of this manufactured scaffold was too high, which made it too rigid for use in regeneration of flexible tissues.

EXAMPLE 5

According to the same manufacturing process as in Example 3, a glycolide/ε-caprolactone copolymer 18.326 g was manufactured by using glycolide of 3.869 g and ε-caprolactone of 15.221 g with a catalyst of stannous octoate of 0.0090 g diluted in toluene of 0.064 ml (yield: 96.0%).

From the GPC analysis in that chloroform was used as a mobile phase solvent with a flow rate of 1 ml/min at 30° C., weight-average molecular weight and distribution of molecular weight of the copolymer were identified to be about 184,000 and 1.84, respectively. Analyzed by the $^1$H-NMR method, the molar ratio of glycolide:ε-caprolactone in the copolymer was 2.0:8.0, and determined through the DSC, the glass transition temperature (Tg) and the melting point were −46.4° C. and 23.1° C, respectively.

Using the copolymer as manufactured above, a porous scaffold having porosity of 95% and pore size of ψ 200~300 μm was manufactured according to the same manufacturing process as in Example 2.

SEM analysis on the pore size and pore distribution of the porous scaffold as manufactured above, showed that the shape and distribution of the pores of the outer surface and internal section of the scaffold were almost identical, and pore size was similar to the size of salt particle.

According to the same measuring method as in Example 2, the mechanical properties of the scaffold were determined. The elongation, the tensile strength and the modulus were 297%, 2.01 Mpa and 1.09 Mpa, respectively.

EXAMPLE 6

Using the same method of making as in Example 3, a glycolide/ε-caprolactone copolymer of 18.419 g was manufactured by reacting glycolide of 9.673 g and ε-caprolactone of 9.513 g in the presence of stannous octoate of 0.0090 g diluted in toluene of 0.0635 ml (yield: 96.0%).

From the GPC analysis in that chloroform was used as a mobile phase solvent with a flow rate of 1 ml/min at 30° C., weight-average molecular weight and distribution of molecular weight of the copolymer were identified to be about 195,000 and 1.62, respectively. Analyzed by the $^1$H-NMR method, the molar ratio of glycolide:ε-caprolactone in the copolymer was 5.1:4.9, and determined through the DSC, the glass transition temperature (Tg) was −19.3° C.

Using the copolymer as manufactured above, a porous scaffold having porosity of 95% and pore size of ψ 200~300 μm was manufactured according to the same manufacturing process as in Example 2.

According to SEM analysis on the pore size and pore distribution of the porous scaffold as manufactured above, shape and distribution of pore of outer surface and internal section of the scaffold were almost identical, and the pore size of the scaffold was similar to the size of salt particle.

Using the same measurement method as in Example 2, the mechanical properties of the scaffold were determined. The elongation, the tensile strength and the modulus were 430%, 0.59 Mpa and 0.15 Mpa, respectively.

The porous scaffold made from the glycolide/ε-caprolactone copolymer of this example has remarkably low modulus and, thus it shows relatively high flexibility compared with that of the porous scaffold made from the lactide/glycolide copolymers as in Examples 1 and 2.

EXAMPLE 7

The same manufacturing protocol as in Example 3 was used to make a glycolide/ε-caprolactone copolymer of 13.878 g by reacting glycolide of 11.608 g and ε-caprolactone of 7.611 g in the presence of stannous octoate of 0.0090 g diluted in toluene of 0.0635 ml (yield: 72.21%).

From the GPC analysis in that chloroform was used as a mobile phase solvent with a flow rate of 1 ml/min at 30° C., weight-average molecular weight and distribution of molecular weight of the copolymer were identified to be about 114,000 and 2.15, respectively. Analyzed by the $^1$H-NMR method, the molar ratio of glycolide:ε-caprolactone in the copolymer was 5.8:4.2, and determined through the DSC, the glass transition temperature (Tg) was −7.42° C.

Using the copolymer as manufactured above, a porous scaffold having porosity of 95% and pore size of ψ 200~300 μm was manufactured according to the same manufacturing process as in Example 2.

According to SEM analysis on the pore size and pore distribution of the porous scaffold as manufactured above, shape and distribution of pore of outer surface and internal section of the scaffold were almost identical, and the pore size of the scaffold was similar to the size of salt particle.

Using the same measurement method as in Example 2, the mechanical properties of the scaffold were determined. The elongation, the tensile strength and the modulus were 187%, 1.84 Mpa and 0.96 Mpa, respectively.

EXAMPLE 8

According to the same manufacturing process as in Example 3, a glycolide/ε-caprolactone copolymer was manufactured by reacting glycolide of 15.477 g and ε-caprolactone of 3.805 g in the presence of stannous octoate of 0.0090 g diluted in toluene of 0.0635 ml.

After the copolymer as manufactured above was dissolved in hexafluoroisopropanol, it was precipitated in methanol to remove unreacted monomers. Copolymer of 18.723 g was obtained (yield: 97.09%). Intrinsic viscosity of the collected copolymer was 1.53 dl/g when it was measured from 0.5 g/dl hexafluoroisopropanol solution at 25° C. Analyzed by the $^1$HNMR method, the molar ratio of glycolide:ε-caprolactone in the copolymer was 8.0:2.0, and determined through the DSC, the glass transition temperature (Tg) and the melting point were −3.40° C. and 216.9° C., respectively.

Using the above copolymer, a porous scaffold having porosity of 95% and pore size of ψ 200~300 μm was manufactured according to the same manufacturing process as in Example 2.

Upon SEM analysis on pore size and distribution of the porous scaffold as manufactured above, the shapes and distribution of pores of the outer surface and internal section of the scaffold were found to be almost identical, and pore size was similar to the size of salt particle.

According to the same measuring method as in Example 2, the mechanical properties of the scaffold were determined. The elongation, the tensile strength and the modulus were 75%, 2.51 Mpa and 1.56 Mpa, respectively.

EXAMPLE 9

Using the glycolide/ε-caprolactone copolymer manufactured as in Example 6, a porous scaffold having pore size of ψ 200~300 μm was manufactured according to the same manufacturing process as in Example 2 except that the porosity thereof was 60%.

According to SEM analysis on the pore size and pore distribution of the porous scaffold as manufactured above, shape and distribution of pore of outer surface and internal section of the scaffold were almost identical, and pore size was similar to the size of salt particle.

According to the same measuring method as in Example 2, the mechanical properties of the scaffold were determined. The elongation, the tensile strength and the modulus were 1266%, 2.51 Mpa and 0.87 Mpa, respectively.

EXAMPLE 10

Using the glycolide/ε-caprolactone copolymer manufactured as in Example 6, a porous scaffold having pore size of ψ 200~300 μm was manufactured according to the same manufacturing process as in Example 2 except that the porosity thereof was 98.0%.

According to SEM analysis on the pore size and pore distribution of the porous scaffold as manufactured above, shape and distribution of pore of outer surface and internal section of the scaffold were almost identical, and pore size was similar to the size of salt particle.

Using the same measurement method as in Example 2, the mechanical properties of the scaffold were determined. The elongation, the tensile strength and the modulus were 401%, 0.39 Mpa and 0.11 Mpa, respectively.

EXAMPLE 11

Using the glycolide/ε-caprolactone copolymer manufactured as in Example 6, a porous scaffold having porosity was 95% was manufactured according to the same manufacturing process as in Example 2 except that the pore size of ψ 300~500 μm.

Upon SEM analysis on the pore size and distribution of the porous scaffold as manufactured above, shape and distribution of pore of outer surface and internal section of the scaffold were almost identical, and pore size was similar to the size of salt particle.

Using the same measuring method as in Example 2, the mechanical properties of the scaffold were determined. The elongation, the tensile strength and the modulus were 289%, 0.41 Mpa and 0.10 Mpa, respectively.

EXAMPLE 12

Using the glycolide/ε-caprolactone copolymer manufactured as in Example 6, a porous scaffold having porosity of 95% was manufactured according to the same manufacturing process as in Example 2 except that the pore size of ψ 600~800 μm.

With SEM analysis, the pore size and distribution of the porous scaffold as manufactured above, was determined to have a shape and distribution of outer surface and internal section of the scaffold almost identical, and pore size was similar to the size of salt particle.

According to the same measuring method as in Example 2, the mechanical properties of the scaffold were determined. The elongation, the tensile strength and the modulus were 125%, 0.23 Mpa and 0.06 Mpa, respectively.

EXAMPLE 13

The glycolide/ε-caprolactone copolymer of 7.0 g manufactured as in Example 6 was put in a vial and dissolved in chloroform of 30 ml. This chloroform solution was filtered by means of a 0.45 μm membrane filter, and then it was poured into a well-fitted petri dish. A sheet type film having the thickness of 1 mm was manufactured by gradually removing the solvent at low temperature. Furthermore, the manufactured film was rolled in a circular Teflon mold and joined together by means of chloroform to manufacture a tube type film. Mechanical properties of the manufactured sheet type film were measured. The elongation, the tensile strength and the modulus were 500%, 5.23 Mpa and 1.5 Mpa, respectively. Both the sheet type film and the tube type film have the elasticity as described above and they are used for regeneration of a duct type tissue such as the urethral canal.

Tables 1 and 2 denote the thermal characteristics and molecular weight of the copolymers as manufactured according to Examples 2 to 4 and Examples 5–12, and the mechanical properties of scaffolds manufactured from to the copolymer.

Figure 1:
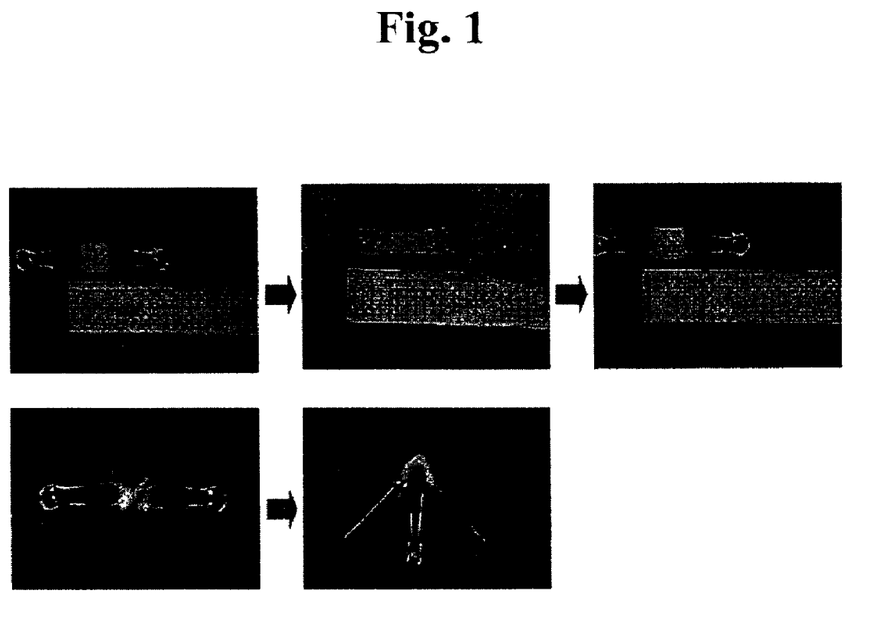
FIG. 1 is a set of photographs showing transformation and elasticity characteristics of the porous scaffold manufactured by using the glycolide/ε-caprolactone copolymer of the present invention.
Figure 2:
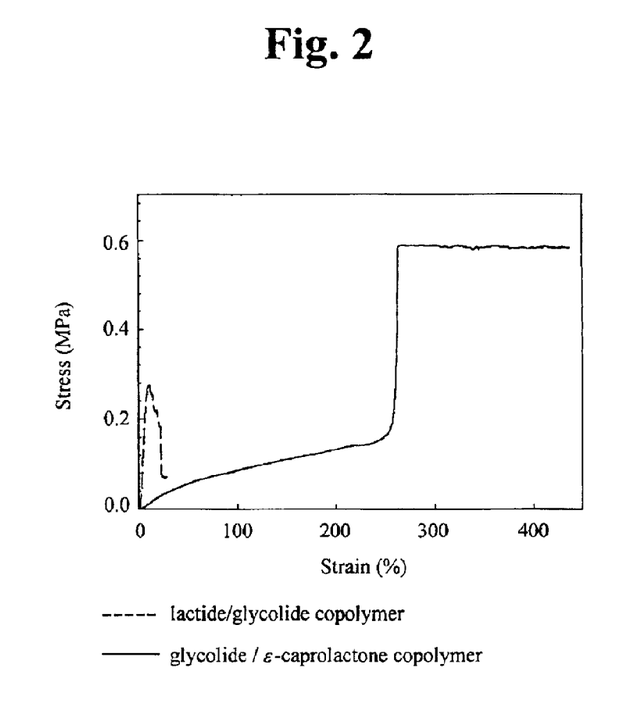
FIG. 2 is a graph showing data on mechanical properties for the porous scaffold made from the glycolide/ε-caprolactone copolymer and a scaffold made from a lactide/glycolide copolymer.
Figure 3A:
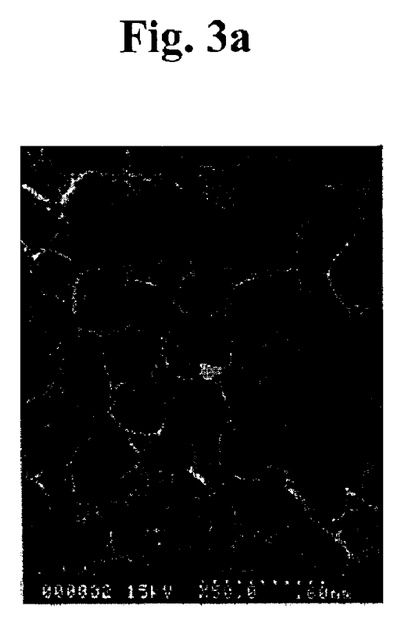
FIG. 3a shows a scaffold with pore sizes ≦200 μm and porosity of 93%.
Figure 3B:
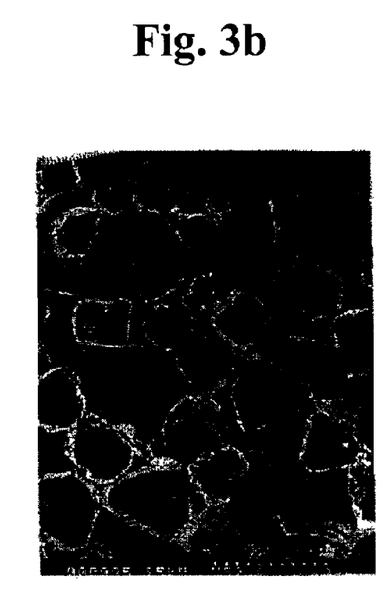
FIG. 3b shows a scaffold with pore sizes of about 200 to 300 μm and porosity of 93%.
Figure 3C:
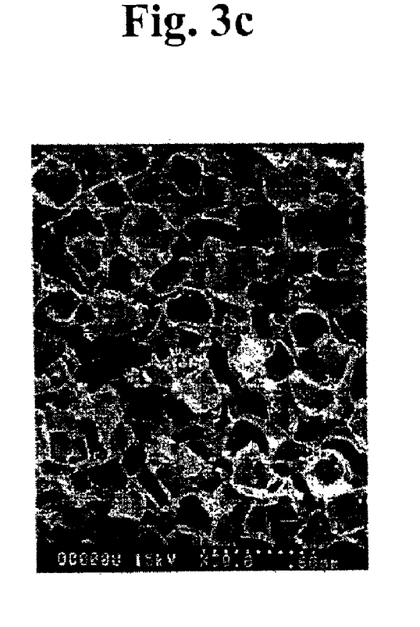
FIG. 3c shows a scaffold with pore sizes of about 200 to 300 μm and porosity of 95%.
Figure 3D:
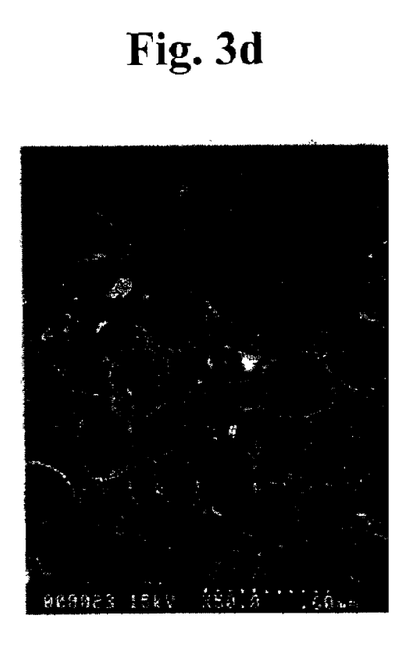
FIG. 3d shows a scaffold with pore size of about 200 to 300 μm and porosity of 98%.

As shown in Table 1, below, the porous scaffolds made from a lactide/glycolide copolymer of Example 2 have the modulus higher than those made from the copolymers of the present invention, and thus, are rigid. FIG. 2 is a graph for comparing mechanical properties of porous scaffolds made from the glycolide/ε-caprolactone copolymer in accordance with the present invention with those of scaffolds made from the lactide/glycolide copolymer.

Furthermore, if the composition ratio of one of glycolide monomer or ε-caprolactone monomer was too high, the modulus thereof becomes excessively high and the porous scaffold made therefrom also becomes too rigid.

TABLE 1

Characteristics of scaffolds according to kinds of copolymers and variation in composition ratio thereof: Porosity 95%, Pore size ψ 200~300 μm.

| Examples | | Composition Molar Ratio[a] | $T_g$[b] (°C.) | $T_m$[b] (°C.) | Weight-average molecular weight[c] | Distribution of $MW$[c] | Intrinsic Viscosity[d] | Elongation (%) | Tensile Strength (MPa) | Modulus (MPa) |
|---|---|---|---|---|---|---|---|---|---|---|
| Exam. | 2 | [LA]/[GL] 6.0/4.0 | 52.94 | — | 226,000 | 1.50 | — | 28 | 0.28 | 2.50 |
| | 3 | [GL]/[CL] 1.0/9.0 | −53.2 | 58.0 | 213,000 | 1.64 | — | 920 | 0.07 | 0.368 |
| | 4 | [GL]/[CL] 9.0/1.0 | 22.7 | 217.1 | — | — | 1.68 | 19 | 0.85 | 5.01 |
| Exam. | 5 | [GL]/[CL] 2.0/8.0 | −46.4 | 23.1 | 184,000 | 1.84 | — | 297 | 2.01 | 1.09 |
| | 6 | [GL]/[CL] 5.1/4.9 | −19.3 | — | 195,000 | 1.62 | — | 430 | 0.59 | 0.15 |
| | 7 | [GL]/[CL] 5.8/4.2 | −7.42 | — | 114,000 | 2.15 | — | 187 | 1.84 | 0.96 |
| | 8 | [GL]/[CL] 8.0/2.0 | −3.40 | 216.9 | — | — | 1.53 | 75 | 2.51 | 1.56 |

[a] Molecular ratio measured by $^1$H-NMR method
LA: lactide, GL: glycolide, CL: caprolactone
[b] DSC: Heating rate 10° C./min
[c] GPC: chloroform 1 ml/min 30° C.
[d] 0.5 g/dl 25° C. hexafluoroisopropane solution

TABLE 2

Mechanical properties of scaffolds depending on variation in pore size and porosity.

| Examples | Composition Molar Ratio[a] | Porosity[b] (%) | Pore Size[b] (μm) | Elongation (%) | Tensile Strength (MPa) | Modulus (MPa) |
|---|---|---|---|---|---|---|
| 9 | [GL]/[CL] 5.1/4.9 | 60 | 200~300 | 1266 | 2.51 | 0.87 |
| 10 | | 98 | 200~300 | 401 | 0.39 | 0.11 |
| 11 | | 95 | 300~500 | 289 | 0.41 | 0.10 |
| 12 | | 95 | 600~800 | 125 | 0.23 | 0.06 |

[a] Molar ratio measured by $^1$H-NMR method
GL: glycolide, CL: caprolactone
[b] Value measured from the weight of salt particle The biodegradable porous scaffold for tissue engineering made from the glycolide/ε-caprolactone copolymer of the present invention can easily transform its physical shape as it is more flexible than those conventional biodegradable polymers. The material also has excellent elasticity so that it can overcome limitations of mechanical properties of the conventional biodegradable polymers. Further, the scaffold is advantageous for tissue regeneration during culturing the cell tissue as the cells are provided with mechanical stimulation through the scaffold, which makes the cells stronger. Therefore, the biodegradable porous scaffold made from the elastic glycolide/ε-caprolactone copolymer of the present invention is very useful for regeneration of tissue with desired shape and which especially requires flexibility and elasticity.

While the present invention has been shown and described with respect to particular examples, it will be apparent to those skilled in the art that many changes and modifications may be made without departing form the spirit and scope of the invention as defined in the appended claims.

What is claimed is:

1. A porous scaffold for tissue engineering made from a biodegradable glycolide/ε-caprolactone copolymer having a repeat unit of:

wherein:
x and y are integers greater than or equal to 18;
the copolymer has an average molecular weight of about 10,000 daltons; and
the molar ratio of glycolide:ε-caprolactone in the copolymer is 4.0:6.0 to 6.0:4.0.

2. The porous scaffold of claim 1, having a pore size of about 1 to 800 μm.

3. The porous scaffold of claim 1, having a porosity of about 50% to 99%.

4. The porous scaffold of claim 1, having a pore size of about 200 to 500 μm and porosity of about 93% to 96%.

5. The porous scaffold of claim 1, for use in tissue cell cultures and tissue regeneration.

* * * * *